(12) United States Patent
Reynolds et al.

(10) Patent No.: US 11,162,904 B2
(45) Date of Patent: Nov. 2, 2021

(54) ENHANCED COLORIMETRIC APPARATUS AND METHOD FOR EXPLOSIVES DETECTION USING IONIC LIQUIDS

(71) Applicant: LAWRENCE LIVERMORE NATIONAL SECURITY, LLC, Livermore, CA (US)

(72) Inventors: John G. Reynolds, San Ramon, CA (US); Lara D. Leininger, Livermore, CA (US); Thomas W. Myers, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 282 days.

(21) Appl. No.: 16/509,828

(22) Filed: Jul. 12, 2019

(65) Prior Publication Data

US 2021/0010941 A1 Jan. 14, 2021

(51) Int. Cl.
*G01N 21/78* (2006.01)
*G01N 31/22* (2006.01)
*G01N 33/22* (2006.01)

(52) U.S. Cl.
CPC ............. *G01N 21/78* (2013.01); *G01N 31/22* (2013.01); *G01N 33/227* (2013.01)

(58) Field of Classification Search
CPC ....... G01N 21/78; G01N 31/22; G01N 33/227
See application file for complete search history.

(56) References Cited

U.S. PATENT DOCUMENTS

| 7,771,653 | B2 | 8/2010 | Del Eckels et al. |
| 7,867,441 | B2 | 1/2011 | Del Eckels et al. |
| 8,025,856 | B2 | 9/2011 | Nunes et al. |
| 8,765,080 | B1 | 7/2014 | Nunes et al. |
| 2007/0202009 | A1* | 8/2007 | Nunes ............ B01L 3/5023 422/400 |

FOREIGN PATENT DOCUMENTS

EP 1766361 B1 3/2010

OTHER PUBLICATIONS

T. Y-J. Han et al., "The solubility and recrystallization of 1,3,5-triamino-2,4,6-trinitrobenzene in a 3-ethyl-1-methylimidazolium acetate-DMSO cosolvent system", New J. Chem., 2009, 33, 50-56.

* cited by examiner

*Primary Examiner* — Brian R Gordon
*Assistant Examiner* — Dwan A Gerido
(74) *Attorney, Agent, or Firm* — Eddie E. Scott

(57) ABSTRACT

An inspection tester for testing a surface for suspected explosive substances includes a body unit, a breakable ampoule carried by the body unit, and an ionic explosive detecting reagent in the breakable ampoule wherein the body unit and the breakable ampoule are positioned to deliver the ionic explosive detecting reagent to the surface for testing the surface for the suspected explosive substances. The ionic explosive detecting reagent is a salt in a liquid state.

2 Claims, 5 Drawing Sheets

ENHANCED COLORIMETRIC APPARATUS AND METHOD FOR EXPLOSIVES DETECTION USING IONIC LIQUIDS

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to explosives and more particularly to testing for the presence of explosives.

State of Technology

This section provides state of technology information related to the present disclosure. This section state of technology information is not necessarily prior art.

Colorimetric methods are commonly used for detection of explosives. These methods are generally the fastest, least expensive and most overall comprehensive methods for detecting explosives in field situations. However, these methods do not work well with some explosives, particularly, insensitive explosives, such as tri-amino-tri-nitro-benzene (TATB), especially when the molecule is in a polymer-bound formulation.

U.S. Pat. No. 8,025,856 for colorimetric chemical analysis sampler for the presence of explosives provides the state of technology information reproduced below.

Referring now to FIG. 7, details of another embodiment of a lateral flow swab unit are illustrated. This embodiment of a lateral flow swab unit is designated by the reference numeral 701. The lateral flow swab unit 701 comprises polyethylene spheres fused into a lateral flow membrane. The lateral flow swab unit 701 is a Porex Lateral-Flo Membrane. Applicants experimentally determined that the properties of the lateral flow swab unit 701 make it an ideal swipe material for the tester. The lateral flow membrane 701 is chemical resistant, withstands heat as high as 130° C., is durable, is inexpensive, can be formed in any size, and concentrates suspect materials along the solvent front 709 making colorimetric detection limits.

The lateral flow swab unit 701 provides migration of the explosives detecting reagent from the body. This is illustrated by the arrows 703 which show the explosives detecting reagent wicking along the outside surface of the lateral flow swab unit 701. The explosives detecting reagent wicks along the outside surface of the lateral flow swab unit 701 to the surface 702 of the lateral flow swab unit 701. The surface area 702 provides a swipe area for sample collection. The explosives detecting reagent is shown wicking onto the surface 702 as illustrated by the arrows 704. The explosives detecting reagent is delivered to the lateral flow swab unit surface 702. The swab surface 702 is swiped across the surface of the area to be tested. Any suspect substance will be picked up by the swab surface 702. Any suspect matter is concentrated as illustrated at 705 which improves the detection capability of the tester. If the swab surface 702 becomes colored, the test is positive for explosives.

Referring now to FIGS. 8 and 9, two of the colorimetric tests to screen for explosives will be illustrated. The colorimetric chemistry illustrated in FIGS. 8 and 9 incorporates the Meisenheimer complex in FIG. 7 and the Griess Reagent in FIG. 8. The calorimetric chemistry incorporates, but is not limited to, the Meisenheimer complex, the Griess Reagent, Nessler's reagent, and Thymol reaction. The chemistry used in the test for explosives is as follows: 1) Meisenheimer Complex solution is Tetrabutylammonium Hydroxide in Ethanol and gives a color indication for TNT, Tetryl, and Trinitrobenzene. 2) Diphenylamine (DPA) in conc. $H_2SO_4$ gives a color indication for nitramines, nitrate esters, and TATP and other oxidizers (NG, PETN, TATP, RDX, NQ, AN) 3) Nessler's reagent is a solution of mercury (II) iodide, typically around 1.4%, in aqueous potassium and potassium hydroxide iodide and is specific for ammonium cation (AN). 4) Thymol in conc. $H_2SO_4$ gives green color for most nitrate esters. RDX and HMX give a red color.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

Colorimetric methods are commonly used for detection of explosives. These methods are generally the fastest, least expensive and most overall comprehensive methods for detecting ex-plosives in field situations. However, these methods do not work well with some explosives, particularly, insensitive explosives, such as tri-amino-tri-nitro-benzene (TATB), especially when the molecule is in a polymer-bound formulation. The inventors have developed apparatus, methods and systems that improve colorimetric detection of such explosives, using an ionic explosive detecting reagent. The ionic explosive detecting reagent is a salt in a liquid state. The inventors' apparatus, methods and systems rely on a colored indication for positive detection. This circumvents the need of application of detection reagents, such as a strong base dissolved in alcohol, by using a solvent that simply dissolves and detects TATB in one step. The solvent and detected products are also completely environmentally friendly and can be disposed as non-hazardous waste.

The inventors' apparatus, methods and systems are best when used for field detection of TATB and related materials, such as PBX-9502, LX-17, T2 and other polymer-bonded insensitive explosive formulations. Field detection refers to scenarios where access to laboratory equipment for analysis is not desired, limited or impossible. Field detection extends to indoor and outdoor equipment found at military installations, munition manufacturing facilities, explosives testing facilities, scientific measurement facilities, and other facilities handling explosives. Field detection includes swiping equipment and personnel in the field or at facilities; specifically, for equipment, benches, testing chambers, walls, floors, door handles, etc.; for personnel, hands, arms, shoes, backpacks, etc. The inventors' apparatus, methods and systems can also be used in the laboratory or testing facility where direct contamination of surfaces and materials is suspected.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1:
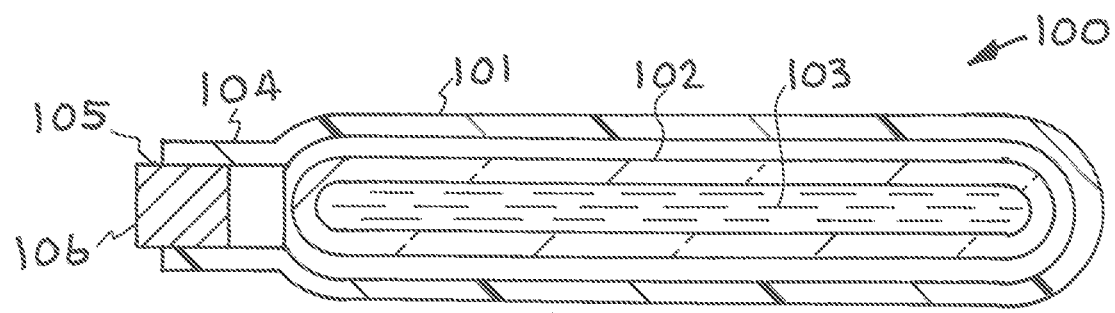
FIGS. 1 and 2 illustrate an embodiment of the inventors' apparatus, systems, and methods for determining the presence of explosives.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Figure 2:
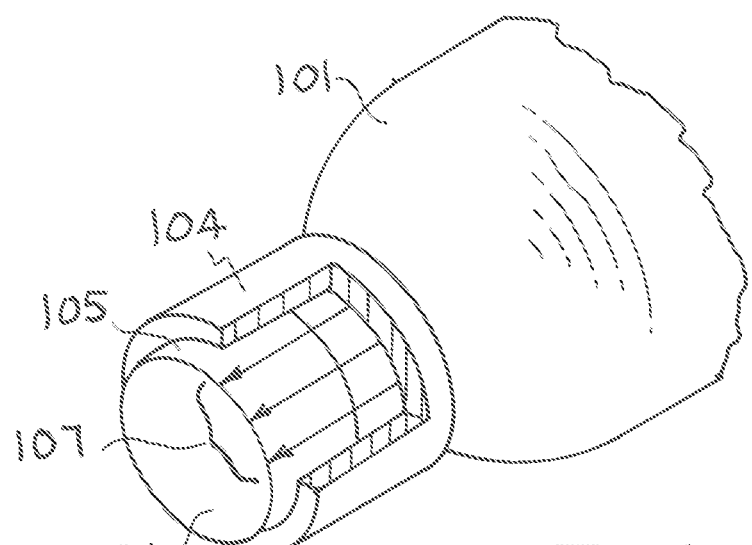

Referring to the drawings, and in particular to FIG. 1 and FIG. 2, an embodiment of the inventor's apparatus, systems, and methods is illustrated. This embodiment is designated generally by the reference numeral 100. FIG. 1 illustrates an explosive tester apparatus, system, and method. The explosive tester 100 is an inexpensive and disposable device. The explosive tester 100 can be used anywhere as a primary screening tool by non-technical personnel to determine whether a surface contains explosives. The explosive tester 100 was developed to allow identification of explosives. This explosive tester can be used by first responders, military, law enforcement, Homeland Security, and other entities.

The explosive tester 100 provides a small, disposable, one use system. The explosive tester 100 uses a simple and rapid method of operation. The structure of the explosive tester 100 includes a body 101. The body 101 is made of a squeezable material such as plastic. An ampoule 102 containing an ionic explosive detecting reagent 103 is located within the squeezable body 101. The explosive detecting reagent 103 is a salt in a liquid state wherein the salt has a melting point below 212° F. In the embodiment 100 the ionic explosive detecting reagent 103 is 3-ethyl-1-methylimidazolium acetate.

An outlet 104 in the body 101 allows the explosives detecting reagent 103 to be dispensed for detecting explosives as will be subsequently described. A lateral flow swab unit 105 is operably positioned in the outlet 104. The ampoule 102 containing the explosives detecting reagent 103 is a breakable ampoule and acts as a dispenser for selectively allowing the explosives detecting reagent 103 to be delivered to the lateral flow swab unit 105.

The lateral flow swab unit 105 comprises a microporous membrane material that provides migration of the explosives detecting reagent 103 from the ampoule 102 and the body 101. Lateral flow membrane materials are known for their use in other fields. Lateral flow membrane material is known for use as blotting techniques, enzyme-linked immunosorbent assay (ELISA) testing, and lateral-flow immunochromatographic tests. The lateral flow swab unit 105 comprises polyethylene spheres fused into a lateral flow membrane.

Referring now to FIG. 2, details of the lateral flow swab unit 105 are illustrated. The lateral flow swab unit 105 is made a microporous membrane material that provides migration of the explosives detecting reagent from the ampoule and the body. This is illustrated by the arrows 107 which show the explosives detecting reagent wicking along the outside surface of the lateral flow swab unit 105. The explosives detecting reagent wicks along the outside surface of the lateral flow swab unit 105 to the surface 106 of the lateral flow swab unit 105. The surface area 106 provides a swipe area for sample collection. The lateral flow swab unit 105 comprises polyethylene spheres fused into a lateral flow membrane. In the embodiment 100 the swab unit 105 is a Porex Lateral-Flo Membrane.

Figure 3:
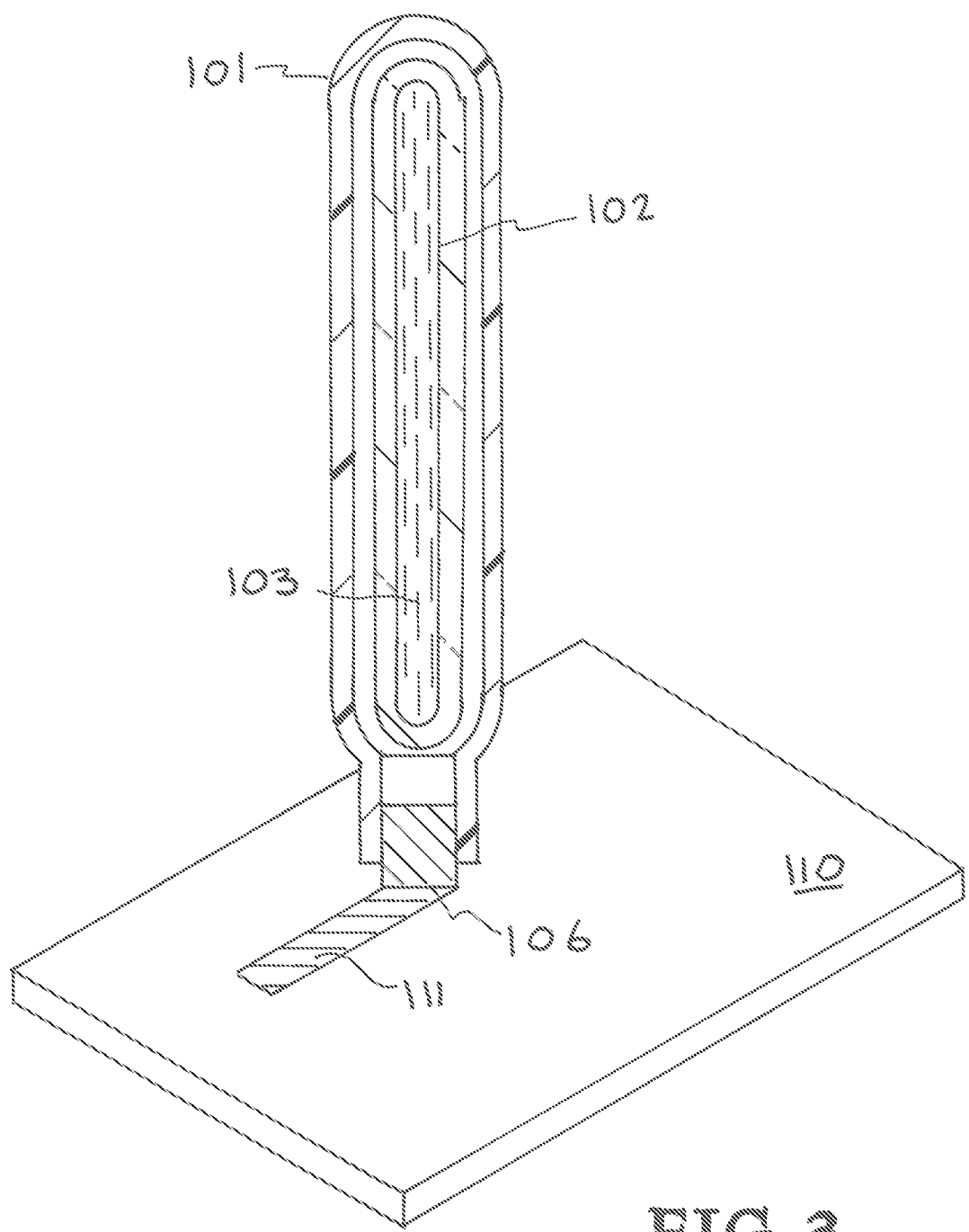
FIGS. 3, 4, and 5 illustrate the operation of the inventors' apparatus, systems, and methods for determining the presence of explosives.
Figure 4:
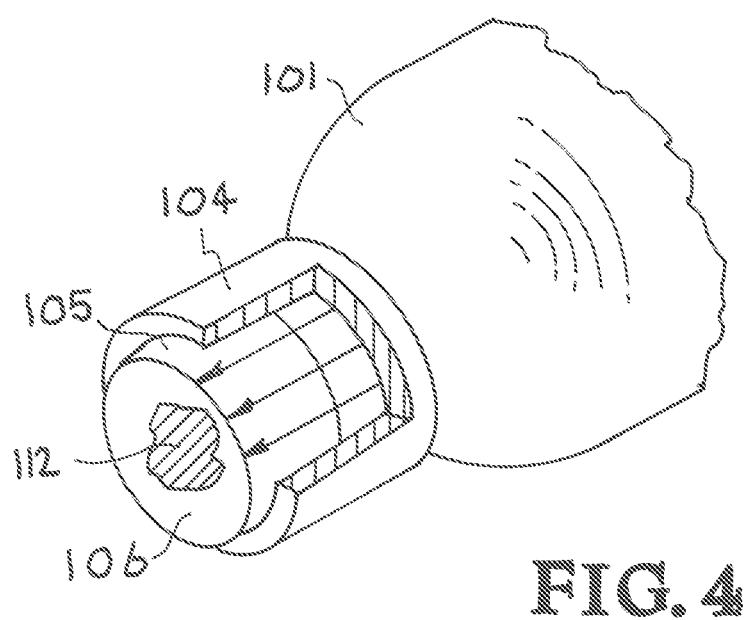
Figure 5:
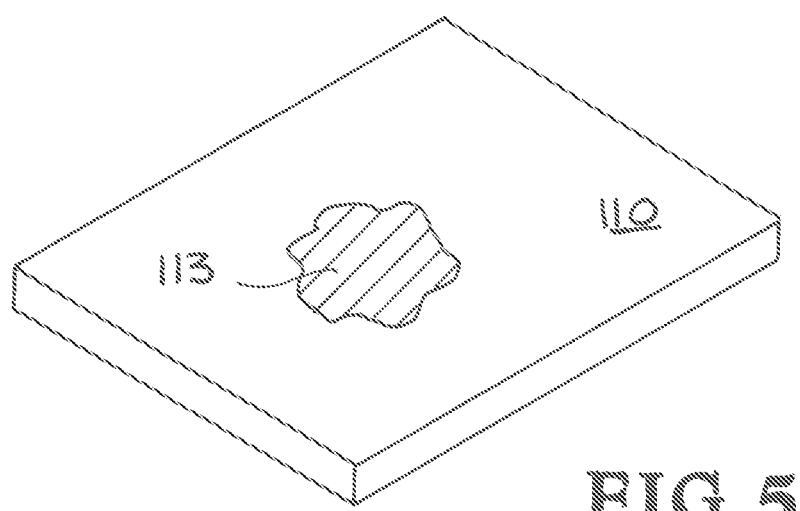

Referring to FIGS. 3, 4, and 5; the operation of the explosives tester 100 is illustrated. As illustrated in FIG. 3, the swab surface 106 of the lateral flow swab unit 101 is exposed to the suspect substance. This is accomplished by the swab surface 106 being swiped across a surface containing the suspect substance. FIG. 3 shows the swab surface 106 being swiped across a suspect surface 110. The explosive detecting reagent 103 has contacted the area 111 of the suspect surface. It should also be noted that articles of explosive material are picked up by the swab surface 106.

The operation of the explosives tester 100 starts by breaking the ampoule 102 containing the explosives detecting reagent 103 located within the squeezable body 101. The explosive detecting reagent 103 is a salt in a liquid state wherein the salt has a melting point below 212° F. In the embodiment 100 the ionic explosive detecting reagent 103 is 3-ethyl-1-methylimidazolium acetate. The explosive detecting reagent 103 is delivered to the swab surface 106 by squeezing the body 101 and breaking the ampoule 102. The ampoule 102 acts as a dispenser allowing the explosives detecting reagent 103 to be delivered to the lateral flow swab unit 101 and the swab surface 106. The swab surface 106 is swiped across the suspect surface 110. Any suspect substance will be picked up by the swab surface 106. As shown in FIG. 3, the explosive detecting reagent 103 has contacted the area 111 of the suspect surface 110.

Referring now to FIG. 4, any suspect substance on surface 110 will be picked up by the swab surface 106 and the ionic explosive detecting reagent has been delivered to the swab surface 106. If the swab surface 106 becomes colored, the test is positive for explosives. FIG. 4 shows that the area 112 of the swab surface 106 has become colored and the test is positive for explosives.

Referring now to FIG. 5, the ionic explosive detecting reagent 103 has been delivered to the swab surface 106 and onto the suspect surface 110. Any suspect substance on the suspect surface 110 will be contacted by the ionic explosive detecting reagent 103. If the suspect surface 110 becomes colored, the test is positive for explosives. FIG. 5 shows that the area 113 of the suspect surface 110 has become colored and the test is positive for explosives.

The explosives tester 100 provides a small, disposable, one use system. The explosives tester 100 uses a simple and rapid method of operation. The explosives tester 100 is an inexpensive and disposable device. The explosives tester 100 can be used anywhere as a primary screening tool by non-technical personnel to determine whether a surface contains explosives. The explosives tester 100 allows identification of explosives. This explosives tester can be used by first responders, military, law enforcement, Homeland Security, and others.

Figure 6:
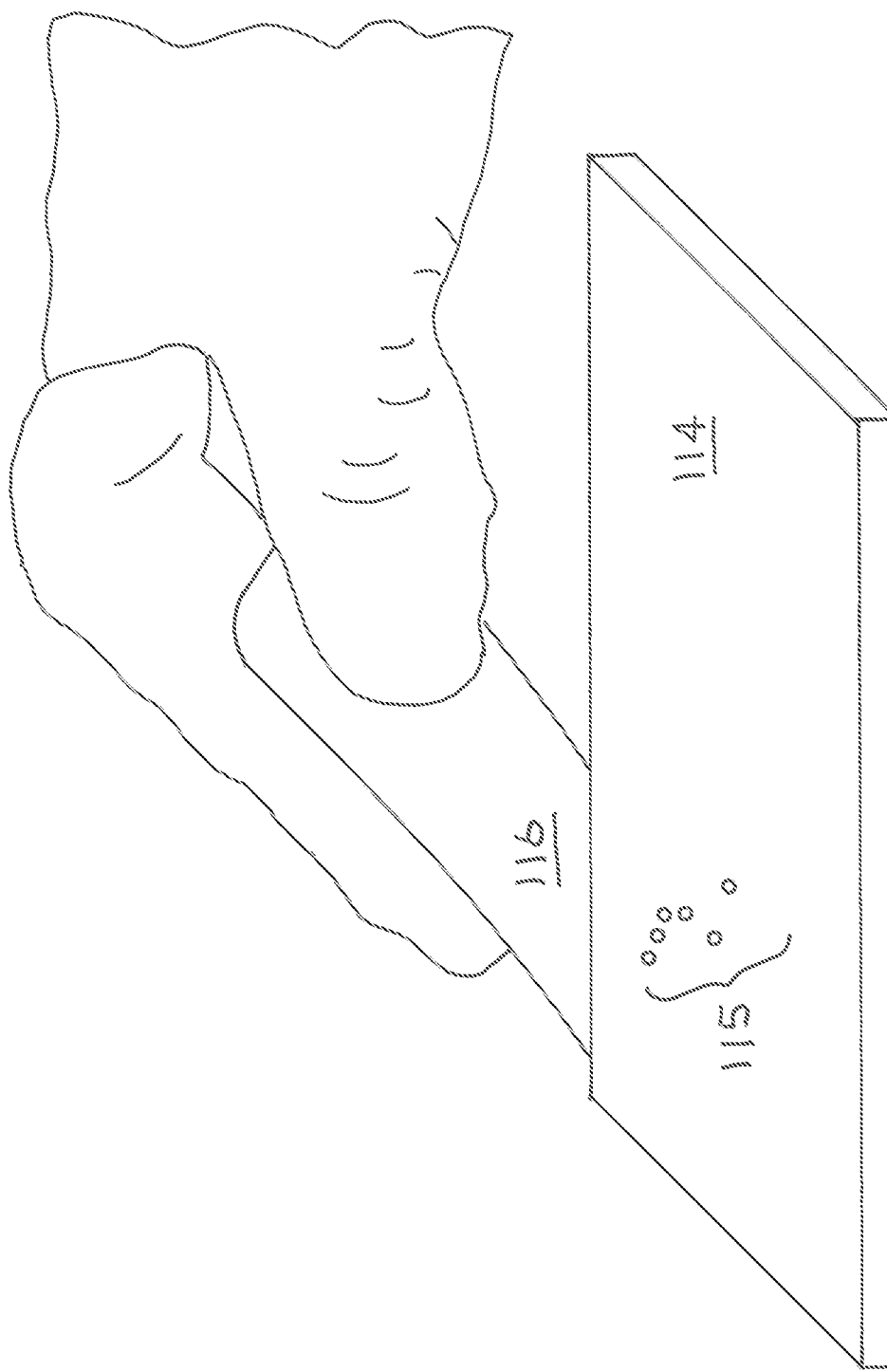
FIGS. 6, 7, and 8 illustrate another embodiment of the inventors' apparatus, systems, and methods for determining the presence of explosives.
Figure 7:
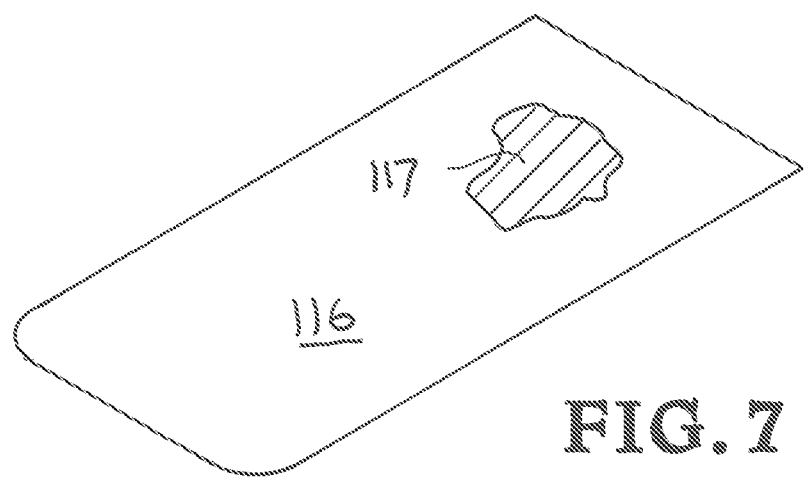
Figure 8:
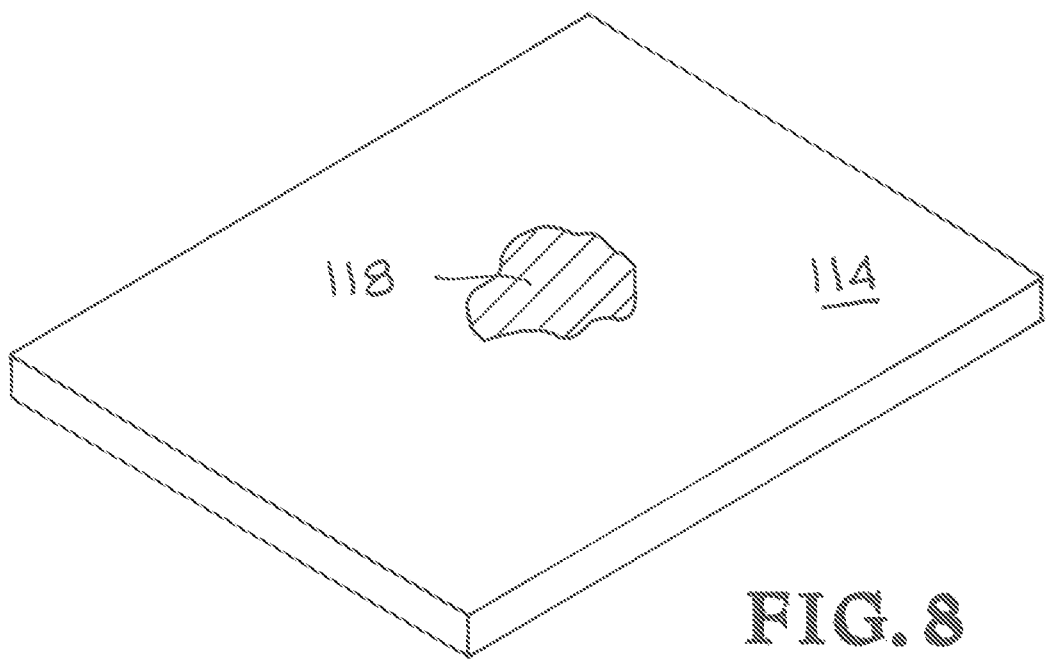

Referring to FIGS. 6, 7, and 8 another embodiment of the inventors' apparatus, systems, and methods for determining the presence of explosives is illustrated. FIG. 6 shows a swab sample pad 116 being positioned to be swiped across a surface 114 containing a suspect substance 115. The swab sample pad 116 can be saturated with the ionic explosive detecting reagent before being swiped or the swab sample pad 116 can be dry swiped across the surface 114 containing a suspect substance 115 and the ionic explosive detecting reagent added afterward. The explosive detecting reagent is a salt in a liquid state wherein the salt has a melting point below 212° F.

FIG. 7 shows the swab sample pad 116 after it has been saturated with the ionic explosive detecting reagent and swiped across the surface 114. This will cause any explosives residue to be collected and held by the swab sample pad 116. If the swab sample pad 116 becomes colored, the test is positive for explosives. FIG. 7 shows that the area 117 of the swab sample pad 116 has become colored and the test is positive for explosives.

Referring now to FIG. 8, the ionic explosive detecting reagent has been delivered to the surface of the swab sample pad 116 and onto the surface 114 containing a suspect substance 115. Any suspect substance on the suspect surface 114 will be contacted by the ionic explosive detecting reagent. If the suspect surface 114 becomes colored, the test is positive for explosives. FIG. 8 shows that the area 118 of the suspect surface 114 has become colored and the test is positive for explosives.

The explosives tester provides a small, disposable, one use system. The explosives tester uses a simple and rapid method of operation. The explosives tester is an inexpensive and disposable device. The explosives tester can be used anywhere as a primary screening tool by non-technical personnel to determine whether a surface contains explosives. The explosives tester allows identification of explosives. This explosives tester can be used by first responders, military, law enforcement, Homeland Security, and others.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. An inspection tester apparatus for testing a surface for suspected explosive substances, comprising:
    a body unit,
    a breakable ampoule carried by said body unit, and
    an ionic explosive detecting reagent in said breakable ampoule,
    wherein said ionic explosive detecting reagent is a salt in a liquid state,
    wherein said salt has a melting point below 212° F.,
    wherein said ionic explosive detecting reagent is 3-ethyl-1-methylimidazolium acetate, and
    wherein said body unit and said breakable ampoule are positioned to deliver said ionic explosive detecting reagent to the surface for testing the surface for the suspected explosive substances.

2. An inspection tester apparatus for testing a surface for suspected explosive substances, comprising:
- a cylindrical body unit made of a squeezable material;
- a breakable ampoule inside of said cylindrical body unit;
- an ionic explosives detecting reagent inside of said breakable ampoule,
- wherein said ionic explosive detecting reagent is a salt in a liquid state,
- wherein said salt has a melting point below 212° F.,
- wherein said ionic explosive detecting reagent salt is 3-ethyl-1-methylimidazolium acetate, and
- wherein said cylindrical body unit and said breakable ampoule are positioned to deliver said ionic explosive detecting reagent to the surface for testing the surface for the suspected explosive substances.

* * * * *